United States Patent [19]
Johanson et al.

[11] Patent Number: 4,719,809
[45] Date of Patent: Jan. 19, 1988

[54] APPARATUS AND TEST METHOD FOR DETERMINING FLOW OR NO FLOW CONDITIONS OF BULK SOLIDS

[75] Inventors: Jerry R. Johanson; Kerry D. Johanson, both of San Luis Obispo, Calif.

[73] Assignee: JR Johanson, Inc., San Luis Obispo, Calif.

[21] Appl. No.: 922,009

[22] Filed: Oct. 21, 1986

Related U.S. Application Data

[63] Continuation-in-part of Ser. No. 815,226, Dec. 31, 1985, abandoned.

[51] Int. Cl.⁴ .............................................. G01N 11/00
[52] U.S. Cl. ............................................ 73/866; 73/823
[58] Field of Search ................ 73/822, 823, 818, 863, 73/73, 866, 865.6, 760, 788

[56] References Cited

U.S. PATENT DOCUMENTS

| | | | |
|---|---|---|---|
| 2,633,027 | 3/1953 | Bunnell | 73/866 |
| 3,216,242 | 11/1965 | Eyrich | 73/823 |
| 3,221,560 | 12/1965 | Kosa et al. | 73/866 |
| 3,478,572 | 11/1969 | McRae et al. | 73/823 |
| 3,638,478 | 2/1972 | Dietert et al. | 73/823 |
| 3,665,768 | 5/1972 | Hosokawa et al. | 73/866 |
| 3,890,830 | 6/1975 | Dyck | 73/73 |
| 3,998,090 | 12/1976 | Wislocki | 73/823 |
| 4,181,023 | 1/1980 | Clamroth et al. | 73/866 |
| 4,274,286 | 6/1981 | Gioia | 73/866 |

FOREIGN PATENT DOCUMENTS

| | | | |
|---|---|---|---|
| 204503 | 5/1968 | U.S.S.R. | 73/823 |
| 258730 | 10/1970 | U.S.S.R. | 73/823 |
| 381949 | 8/1973 | U.S.S.R. | 73/760 |

OTHER PUBLICATIONS

Birks, "The Direct Measurement of the Failure Function of a Cohesive Powder", Powder Tech. (Switz), vol. 4, No. 6, Sep. 1971, pp. 328–337.

*Primary Examiner*—Stewart J. Levy
*Assistant Examiner*—Robert R. Raevis
*Attorney, Agent, or Firm*—Daniel C. McKown

[57] ABSTRACT

Apparatus and a test method for bench scale determination of whether a particulate material will flow under the action of gravity alone from an outlet in the bottom of a container. The apparatus includes a test cell having inclined conical side walls, and that is closed at its larger end by a plug having an inwardly-facing surface that is concave and conforms to a coaxial cone. In this way, cylindrical surfaces are avoided, and the shape of the space within the test cell offers minimal interference with the plastic stress field of the material. This testing method includes the novel step of inverting the test cell after consolidation of the test material but prior to application of the failure load.

18 Claims, 4 Drawing Figures

APPARATUS AND TEST METHOD FOR DETERMINING FLOW OR NO FLOW CONDITIONS OF BULK SOLIDS

BACKGROUND OF THE INVENTION

REFERENCE TO COPENDING APPLICATION

This application is a continuation-in-part of U.S. patent application Ser. No. 815,226 filed Dec. 31, 1985, now abandoned. The benefit of that filing date is claimed for subject matter common to that application and the present application.

FIELD OF THE INVENTION

The present invention is in the field of bulk particulate solids and more specifically relates to an apparatus and testing method for determining on the basis of bench scale testing whether particulate material will flow under the action of gravity through an outlet in the bottom of a container.

THE PRIOR ART

Bulk solids in a divided state such as flour, sugar, ores, dry chemicals and coal are generally handled in silos or containers that require gravity flow for discharge. One of the problems of designing such containers is sizing of the outlet so that the solids do not form an obstruction by arching across the outlet.

The size of outlet required to prevent arching is a function of the unconfined yield strength of the material, the density of the material, and the shape of the outlet.

There are basically two methods for determining this critical dimension. First, one could construct a full size hopper, load it with the material, and observe whether flow takes place from the outlet. The other approach known in the art is to measure the unconfined yield strength, and then to use this unconfined yield strength as a function of consolidation pressure to analyze the results to predict the hopper outlet dimension. This latter approach has been described in the following technical papers: Jenike, A. W., P. J. Elsey, and R. H. Woolley. "Flow Properties of Bulk Solids." Proc. Amer. Soc. Test. Mater. 60:1168–1181, 1960; Jenike, A. W. "Gravity Flow of Bulk Solids." Univ. of Utah Engineering Experiment Station Bulletin No. 108, 1961; Johanson, J. R. "Know Your Material—How to Predict and Use the Properties of Bulk Solids." Chem. Eng., Oct. 30, 1978, pp. 9–17.

This latter method is usually accomplished by means of a direct shear tester and therefore it is rather cumbersome and time-consuming to obtain the results. A quicker and easier method is needed, particularly for use in the field, where portable testing equipment would be especially handy.

SUMMARY OF THE INVENTION

It is an object of the present invention to provide apparatus and a bench scale test method to determine whether flow will occur through a given outlet under the action of gravity alone.

It is a further object to provide apparatus and a test method for determining the unconfined yield strength of a particulate material.

A further objective is to provide an apparatus and test method that is applicable to conical containers as well as to containers of rectangular horizontal cross section.

These objectives are accomplished by a novel test chamber. The portion of the test chamber in which the material is tested includes no cylindrical walls that contact the material, and in this way the uncertainty associated with the frictional effects of cylindrical walls is eliminated. The side walls of the test chamber conform to the surface of a cone, and the larger end of the conical section is closed by a plug that includes an inwardly facing coaxial concave surface. This unique shape of the test chamber affords minimum interference with the plastic stress field present in the material. During the consolidation phase of the test, the conical walls provide an increasing cross sectional area in the direction of motion so as to minimize the frictional effects of the walls. During the failure phase of the test, the same conical walls provide a decreasing cross sectional area in the direction of motion to insure an arching condition similar to that occurring in a hopper during failure conditions.

In a novel aspect of the testing method, the material to be tested is consolidated in the test cell with the conical end piece at the bottom of the test cell, and then the entire cell including the conical bottom piece is turned upside down for the failure loading portion of the test.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

In the first part of this section, the structure of the apparatus will be described in detail. Next, the methods of using the apparatus in carrying out various tests will be discussed. Finally, several alternative embodiments and variations will be described.

The Apparatus

Figure 1:
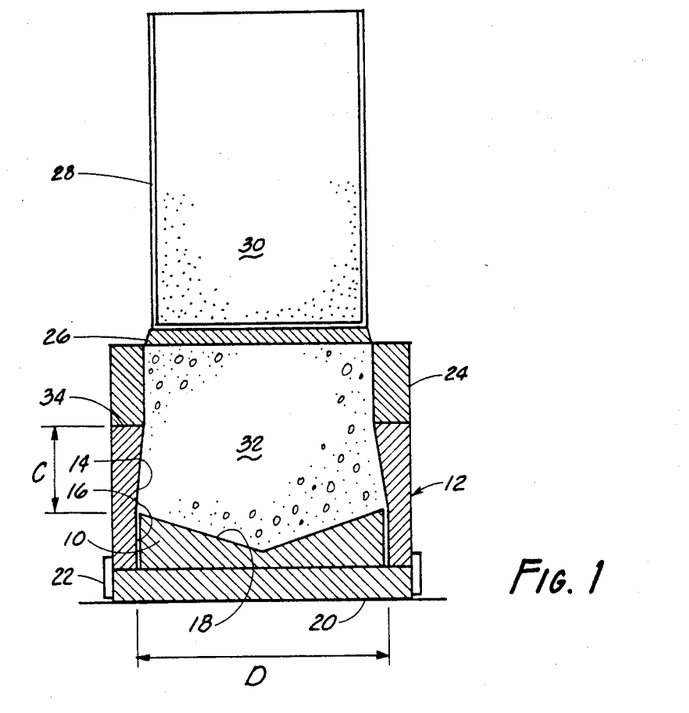
FIG. 1 is an elevation view in cross section showing the apparatus of a preferred embodiment of the present invention at the initial consolidation phase of the test procedure.

Turning now to the drawings in which like parts are denoted by the same reference numeral throughout, there is shown in FIG. 1 a preferred embodiment of the apparatus that is used for performing the tests described below.

The apparatus includes a consolidation base 20 which rests on the floor or on a bench. The conical plug 10 rests on the base 20 with its conical surface 18 facing the inside of the test cell 12. The shape of the space enclosed by the test cell 12 and by the conical plug 10 is an important aspect of the present invention, as will be described below.

The test cell 12 is a unitary sleeve-like part having a conical inside surface 14 shaped to conform to a truncated cone joined at its larger diameter to a cylindrical inside surface 16, which, as seen in FIG. 1, merely serves to locate the plug 10 during the consolidation phase of testing. The conical inside surface 14 is inclined to the vertical by approximately six degrees, so that it could also be said that the cone to which the surface 14 conforms has a vertex angle of twelve degrees, in the preferred embodiment. If the semi-angle is less than four degrees, the convergence will be insufficient to form an arch during the failure step of the test procedure. On the other hand, the angle must not be so great that it becomes imcompatable with the mass flow stress field in the test cell during the failure step of the test procedure. The conical plug 10 is slightly smaller in diameter than the cylindrical inside surface 16 so that the plug 10 can, at a later stage of the test, move freely in the axial direction with respect to the test cell 12. The height of the conical plug 10 in the axial direction is slightly less than the height of the cylindrical inside surface 16 to accommodate some movement by the plug in the axial direction.

The apparatus further includes a mold ring 24 that rests upon the test cell 12 and that has a diameter approximately equal to the diameter of the opening at the top 34 of the test cell.

In a typical test, the test cell 12 and the mold ring 24 are filled with the material 32 under test, and the material 32 is then consolidated to a specific degree.

In the best mode for carrying out the invention, the consolidation is accomplished by placing the flat disk 26 on top of the material 32 under test. The diameter of the flat disk is slightly less than the inside diameter of the mold ring 24 to permit the disk 26 to move downwardly into the mold ring 24 without contacting the mold ring. In the best mode, a consolidation load container 28 is then rested upon the disk 26 and is slowly filled with a particulate ballast material 30 to a specific pre-calculated depth H. All of the parts of the apparatus are made of steel in the preferred embodiment, although in other embodiments any strong durable non-absorbent material may be used.

Because the material in the proposed hopper typically includes a degree of moisture, the material 32 under test also contains moisture, and it is important to prevent the loss of this moisture, since it affects the accuracy of the results. For this reason, a metal or rubber keeper ring 22 tightly encircles the crack between the test cell 12 and the base 20.

Figure 2:
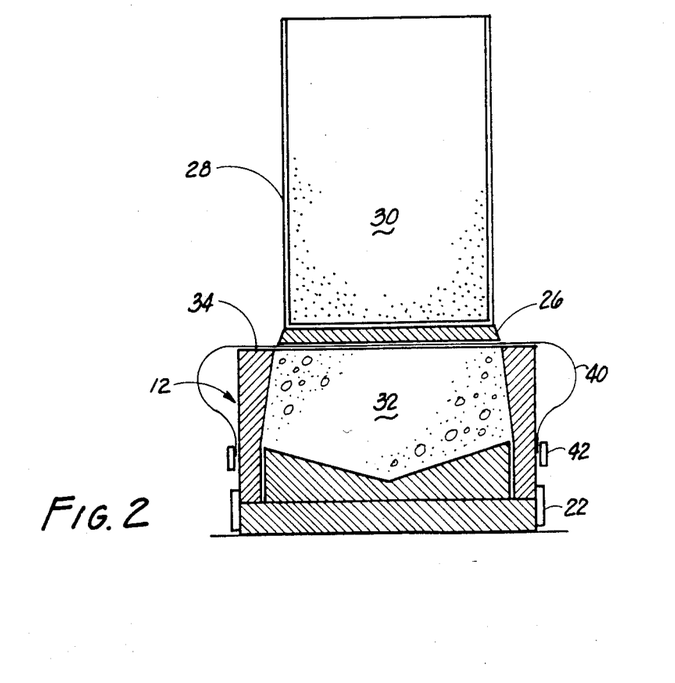
FIG. 2 is an elevation view in cross section showing the apparatus at a later stage of the test procedure.

The length of time during which the consolidation load is applied should approximate the dead time of the material in the proposed hopper, and if this amounts to an appreciable amount of time, it may be essential to take the additional step against moisture loss shown in FIG. 2. In FIG. 2, a moisture seal 40 is inserted between the material 32 under test and the disk 26.

The moisture seal 40 consists of a thin sheet of pliable plastic, which is held in place by the keeper 42. The keeper 42 in a preferred embodiment consists of a band of metal or rubber.

Figure 3:
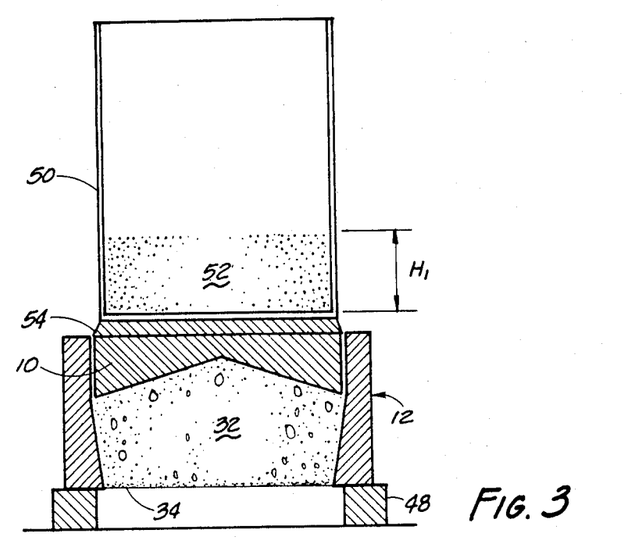
FIG. 3 is an elevation view in cross section showing the apparatus at a later stage of the test procedure; and, FIG. 4 is a perspective view showing a rectangular test apparatus.

FIG. 3 shows the apparatus at a later stage of the test method. After the material being tested has consolidated for the desired length of time, the moisture seals are removed and the test cell 12 is turned upside down and placed on the failure base 48. The failure base 48 is merely a support which does not interfere with the material in the test cell or prevent the material 32 from falling out of the test cell. Note that the FIG. 3, the test cell 12 is upside down relative to its position in FIGS. 1 and 2, and that the conical plug 10 remains in place in the test cell. On top of the conical plug is placed the failure disk 54 which, in a preferred embodiment, is a disk of steel which serves to evenly distribute the applied failure load. The failure load container 50, which is not necessarily the same as the consolidation load container 28, is placed on top of the failure disk 54 and is gradually filled with a ballast material, such as sand, gravel, or water. At some point as additional failure load material 52 is added, the pressure loading on the material 32 becomes too great to resist, and the material 32 collapses and falls out of the test cell 12. The height $H_1$ of the failure load material 52 at the instant of failure is carefully noted and, as will be seen below, is used in calculating the test results.

It will be recognized that the conical shape of the test cell is an important aspect of the invention. During the consolidation phase of testing, shown in FIGS. 1 and 2, this shape provides an increase in area in the direction of flow, insuring a minimum of frictional reaction from the walls of the test cell during the consolidation phase, thereby permitting a nearly uniform and known compaction of the material tested. During the failure phase of testing, shown in FIG. 3, the conical shape of the test cell provides a decreasing cross sectional area in the direction of flow so as to simulate the condition occurring in a full-scale hopper.

The apparatus shown in FIGS. 1-3 is used for determining whether a particulate material in a large container will flow by the action of gravity alone through a circular outlet in the bottom of the container. If, instead of being circular, the outlet is rectangular, the apparatus shown in FIG. 4 may be used. That apparatus is in every sense the rectangular analog of the apparatus shown in FIGS. 1-3.

Figure 4:
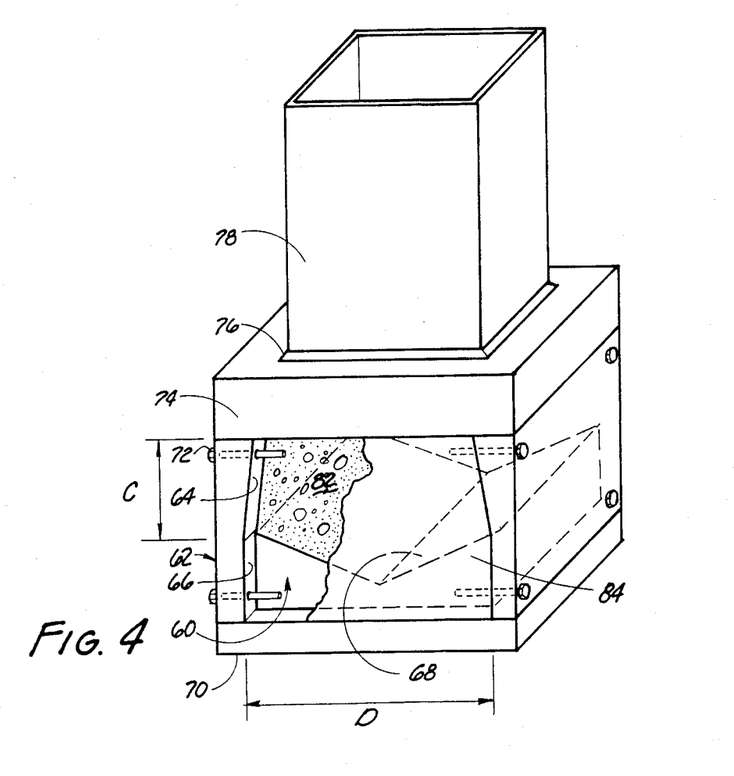

In the apparatus of FIG. 4, a trough-shaped plug 60 having the inclined plane faces 68 extends into the test cell 62. The test cell 62 is rectangular in horizontal cross-section. The right and left walls as shown in FIG. 4 each include a vertical portion 66 and an inclined portion 64. The front and rear walls are vertical only, and are provided with removable panels 84 that are held in place by removable pins of which the pin 72 is typical.

FIG. 4 is comparable to FIG. 1 in that it shows the apparatus in the initial stage of the testing. A rectangular mold frame 74 rests on top of the test cell 62, and is comparable to the mold ring 24 of FIG. 1. A consolidation plate 76 is interposed between the consolidation load container 78 and the material 82 under test. The entire apparatus rests on a consolidation base 70.

With reference to the apparatus of FIGS. 1-4 inclusive, it is essential when testing cohesive solids (defined as those in which the ratio R of the compacting pressure to the instantaneous unconfined yield stress is less than 2.0) that the walls of the converging parts of the test cell have a rough finish and that the height-to-diameter ratio C/D should not exceed 0.2 R. If the ratio exceeds 0.2 R, there is a considerable likelihood that recompaction of the material will occur during failure, thereby giving a false reading. Since the ratio R is seldom less than 1.1 for computing pressures of practical interest, in the preferred embodiment, C/D has been chosen to equal 0.22. For the embodiment shown in FIG. 4, the critical value of C/D is about twice that for the configurations of FIGS. 1-3, and in a preferred embodiment, the ratio C/D is approximately equal to 0.4 R or 0.44 for R=1.1.

This relatively larger allowable value of C for the rectangular test cell can be very important when testing solids with large particles where C must be several times larger than the particle size.

The Method

The test procedure is substantially the same for the embodiments of FIGS. 1 and 4. The apparatus shown and described, when used in accordance with the test procedure given below, can be used to predict whether a circular or rectangular outlet in the bottom of a container partially filled with a particulate material will discharge under the action of gravity alone or whether, instead, arching of the material above the outlet will develop to prevent the desired flow. It will be seen below, that in addition to determining whether or not flow will occur, the method can be used to determine the size of outlet required to prevent arching and, with some minor modifications, can be used to measure the unconfined yield strength of the material under test.

Initially, the test cell 12 with the conical plug 10 are resting on the base 20. The mold ring 24 is assumed to be resting on the test cell 12. The test cell is filled with the material under test to the top of the mold ring. Next, the disk 26 is placed on top of the material 32, the consolidation load container 28 is placed on top of the disk 26, and the consolidation load 30 is poured into the container 28. This causes the material 32 to consolidate, and if the material 32 has consolidated to a level below the top 34 of the test cell, it is necessary to remove the consolidation container, to refill the mold ring 24, and to apply the consolidation load 30 again to the material 32 until the consolidation level does not sink below the top 34 of the test cell.

Next, the mold ring 24 is removed and the material 32 is scraped level with the top 34 of the test cell. Thereafter, the disk 26 and the consolidation load container 28 are replaced as shown in FIG. 2, and the consolidation load 30 is applied and allowed to sit for a time equal to the time at rest of the material within the full-size hopper being simulated. If this time at rest is in excess of a few minutes, it is necessary to cover the test cell with a moisture impermeable seal such as the moisture seal 40 shown in FIG. 2.

When the apparatus is used to test whether or not flow will occur, the appropriate height H of ballast in the consolidation load container 28 is:

$$H = \frac{F}{1+m} \frac{\gamma_1}{\gamma_2} \frac{A_1}{A_2} B - \frac{W_c}{\gamma_2 A_2}$$

where
$\gamma_1$=bulk density of material in test cell
$\gamma_2$=bulk density of ballast material
$A_1$=average of the top and bottom cross sectional areas of test cell
$A_2$=cross sectional area of consolidation load container
$W_c$=weight of the consolidation load container
$B$=diameter of circular outlet of a conical full-size hopper or width of rectangular outlet of a rectangular full-size hopper
$m=1$ for a conical container
$m=0$ for a rectangular container
$F$=overpressure factor.

The overpressure factor F accounts for the additional pessure caused by forces other than gravity that may be operative on the container being simulated. Examples include vibration, the impact of a falling stream of particles entering the container, and the presence of gas pressure gradients within the material in the container such as might be caused by a flow of gas through the solids from top to bottom.

If vibrations cause a peak vertical acceleration of a, then $$F = \left(1 + \frac{a}{g}\right)$$

where g is the acceleration of gravity.

A downwardly acting gas pressure gradient of magnitude dp/dx can be accounted for by setting $$F = \left(1 + \frac{dp/dx}{\gamma}\right)$$

where $\gamma$ is the bulk density of the material in the container and dp/dx is the pressure gradient in the upward direction.

The appropriate expression for F in the presence of a falling stream of particles is derived in "New Design Criteria for Hoppers and Bins" by J. R. Johanson and H. Colijn, Iron & Steel Engineer, October 1964, pp. 85-104.

The major principal consolidation pressure acting in a full-size hopper at a position where the width or diameter is B is given by $$\sigma_c = F \frac{\gamma_1 B}{1+m}$$

and the consolidation load is $$L_c = F \frac{\gamma_1 A_1 B}{1+m} = W_c + \gamma_2 A_2 H$$

After the consolidation time has elapsed, the consolidation load container 28, the disk 26, and the moisture seal 40 are removed and the test cell 12 along with the base 20, and including the conical plug 10 are turned upside down and placed on the failure base 48 in the position shown in FIG. 3. Assuming the material 32 has a measurable cohesion, it should not fall out of the test cell in response to the shocks normally encountered in handling the apparatus, although clearly, shocks are to be avoided. Thereafter, the base 20 is removed and the failure disk 54 and the failure load container 50 are stacked on top of the conical plug 10 as shown in FIG. 3. It is important that the disk 54 and the container 50 do not touch the test cell during the remaining phases of the test.

Next, the failure load 52 is very gradually poured into the failure load container 50 until failure of the material in the load cell occurs. Typically, such failures are rather abrupt and most of the material within the test cell will fall out upon failure. Very little actual movement of the conical plug 10 occurs before failure, and this limited movement is permitted by the clearance between the conical plug 10 and the inside of the test cell. The height $H_1$ of the material 52 within the failure load container 50 at the time of failure is determined by leveling the material in the failure load container 50 and measuring the height $H_1$ shown in FIG. 3.

If this value of height $H_1$ satisfies the following inequality, then flow will occur by gravity from the outlet of diameter B;

$$H_1 \leq \left(\frac{B}{D} - 1 - \frac{W_c}{CA_1\gamma_1}\right) C \frac{A_1}{A_2} \frac{\gamma_1}{\gamma_2}$$

where C is the height of the test cell and D is the diameter of the test cell, as shown in FIG. 1.

As an alternative to increasing the value of $H_1$, the force $L_F$ applied to cause failure could be measured and the critical failure condition could be described by the equation:

$$L_F \leq \left(\frac{B}{D} - 1\right) CA_1\gamma_1$$

The test procedure for the rectangular opening using the apparatus of FIG. 4 is identical to the procedure just described with the exception that the value of m is different from that used for the circular opening, and the symbol B is defined to be the width of the rectangular outlet which has vertical inlet walls or is infinitely long, and D is the width of the rectangular test cell. It is seen that these differences affect only the magnitude of the consolidation load and the calculated value of $H_1$, but do not otherwise affect the steps of the test procedure.

Variations

Sometimes it is desirable to measure the unconfined yield strength of the material as a function of the applied consolidation pressure $\sigma_c$, and this can be done using a relatively minor variation on the above test procedure. The only differences where the unconfined yield strength is to be determined are that the applied consolidation pressure for a given consolidation load $L_c$ is calculated as $\sigma_c$ $$\sigma_c = \frac{L_c}{A_1} + \gamma_1 \frac{C}{2}$$

where the symbols have the same meaning as above, and if the applied load at failure is denoted by $L_F$ then the unconfined yield strength $f_c$ may be calculated by use of the failure equality in equation (2)

$$f_c = \frac{D}{h}\left(\gamma_1 + \frac{L_F}{A_1C}\right)$$

The unconfined yield strength is used by the soil mechanics discipline to describe the pressure applied at the ends of an unconfined cylinder of soil or concrete to initiate failure of the cylinder.

In another minor variation on the method for determining whether bulk solids will or will not flow from an outlet in a container, it is recognized that there are other techniques for applying a consolidation pressure to the material 32 in the test cell. For example, a pneumatic or hydraulic ram could be used, or even a screw jack could be used with a load cell to indicate the force applied.

Regardless of the device used to apply the consolidation pressure, the consolidation pressure should equal $$\sigma_c = F\frac{\gamma_1 B}{1 + m}$$

Likewise the pressure at the time of failure can be determined in other ways than using the failure load container 50 and the failure load 52 of FIG. 3. Alternative devices for applying the failure pressure can be employed consistent with the test method, and as long as the measured pressure at failure does not exceed the following quantity, then flow will occur by gravity alone:

$$\sigma_F = \left(\frac{B}{D} - 1\right) C\gamma_1$$

In yet another variation on the test method, the consolidation load is applied with the apparatus of FIGS. 1 and 2 already in an inverted position. Clearly, a ballast-filled container would not be appropriate, but some form of pneumatic or hydraulic ram or screw jack with a load cell to indicate the applied force could be employed. After the consolidation phase, it would not then be necessary to invert the test cell 12.

Thus, there has been described a novel apparatus for scale-model testing to determine whether or not flow will occur under the action or gravity from a circular or a rectangular outlet in the bottom of a container that is partly filled with particulate matter. The shape of the space within the test cell is of particular significance. The test chamber walls conform to the surface of a cone, and the end of the test chamber is plugged by a concave conical surface. Accordingly, the material under test never contacts a cylindrical wall and this reduces test error caused by the unknown frictional forces that come into play when the material contacts a cylindrical wall. Also, the shape of the test cell is designed to not interfere with the plastic stress field that develops in the sample during testing. Accordingly, the novel shape of the test cell is highly advantageous and results in greater accuracy.

There has also been described in detail a scale model test procedure that allows accurate prediction of whether or not an outlet in the bottom of a container of particulate matter will discharge under the action of gravity alone. This method, which requires the use of the special test apparatus involves the steps of consolidating the material to a specific extent by application of a specific pressure to it and then inverting the test cell prior to determining the pressure required to cause failure of the material.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. A method of bench scale testing to determine the load at which unsupported consolidated particulate material arched over an outlet of diameter B in the bottom of a full-size container will fail by collapsing and flowing through the outlet, said method comprising the steps of:
  (a) providing a test cell that is hollow and that includes a sleeve-like portion having an inside surface conforming to a frustrated conical section of height C, having a smaller-diameter end and a larger-diameter end, the test cell further including a plug spanning the larger-diameter end of the frustrated conical section and sized to fit loosely therein so as to be freely movable a limited distance into the space within the conical section and having a concave conical inwardly-facing surface;
  (b) placing the test cell on a supporting surface with the plug resting on the supporting surface so that the larger-diameter end of the conical section is below its smaller-diameter end;
  (c) filling the test cell completely full with the particulate material;
  (d) consolidating the particulate material within the test cell by applying a downward pressure at the smaller-diameter end of the conical section, so that the direction of motion of the particulate material during consolidation is toward the plug;
  (e) inverting the test cell with the plug and the consolidated particulate material still in it, so that after the inversion the larger-diameter end of the conical section is above its smaller-diameter end;
  (f) applying a gradually-increasing downward load to the plug to produce failure motion of the particulate material toward the smaller-diameter end of the conical section; and
  (g) noting the downward load at which failure occurs.

2. The method of claim 1 wherein the step of consolidating the particulate material further comprises the step of applying a pressure to the particulate material at the smaller-diameter end of the conical section equal to $$\sigma_c = \frac{1}{(1 + m)} F\gamma_1 B$$

where
F = overpressure factor
$\gamma_1$ = bulk density of the particulate material being tested, and
B = inside diameter of the outlet of the full-size container
m = 1 for a conical container
m = 0 for a rectangular container.

3. The method of claim 2 wherein the pressure is applied to the particulate material for an interval of time equal to how long a particulate material in the full-size container has been at rest.

4. A method of bench scale testing to determine whether or not particulate material will flow, after having been at rest for some time, from a full-size container that requires gravity flow for discharge and that has an outlet of diameter B in its bottom, said method comprising the steps of:
  (a) providing a test cell that is hollow and that includes a sleeve-like portion having an inside surface conforming to a frustrated conical section of height C, having a smaller-diameter end and a larger-diameter end, the test cell further including a plug spanning the larger-diameter end of the frustrated conical section and sized to fit loosely therein so as to be freely movable a limited distance into the space within the conical section and having a concave conical inwardly-facing surface;
  (b) placing the test cell on a supporting surface with the plug resting on the supporting surface so that the larger-diameter end of the conical section is below its smaller-diameter end;
  (c) filling the test cell completely full with the particulate material;
  (d) consolidating the particulate material within the test cell by applying a consolidation load $L_c$ uniformly distributed over the particulate material at the smaller-diameter end of the conical section, so that the direction of motion of the particulate material during consolidation is toward the plug, where $$L_c = \tfrac{1}{2} F\gamma_1 A_1 B$$

where
F = overpressure factor,
$\gamma_1$ = bulk density of the particulate material being tested,
$A_1$ = average cross sectional area of the test cell; and,
  (e) inverting the test cell with the plug and the consolidated particulate material still in it, so that after the inversion the larger-diameter end of the conical section is above its smaller-diameter end;
  (f) applying a gradually-increasing downward load to the plug to produce failure motion of the particulate material toward the smaller-diameter end of the conical section;
  (g) noting the downward load $L_F$ at which failure occurs; and,
  (h) determining whether the noted load $L_F$ at which failure occurred is such that $$L_F \leq \left(\frac{B}{D} - 1\right) CA_1\gamma_1$$

where D is the diameter of the larger-diameter end of the conical section, whereby, if it is, then flow from the full-size container will occur by gravity, but if it is not, then flow from the full size container will not occur by gravity.

5. The method of claim 4 wherein the consolidation load $L_c$ is applied to the particulate material for an interval of time equal to how long a particulate material in the full-size container has been at rest.

6. A method of bench scale testing to determine whether or not particulate material will flow, after having been at rest for some time, from a full-size container that requires gravity flow for discharge and that has an outlet of diameter B in its bottom, said method comprising the steps of:
  (a) providing a test cell that is hollow and that includes a sleeve-like portion having an inside surface conforming to a frustrated conical section of height C, having a smaller-diameter end and a larger-diameter end, the test cell further including a plug spanning the larger-diameter end of the frustrated conical section and sized to fit loosely therein so as to be freely movable a limited distance into the space within the conical section and having a concave conical inwardly-facing surface;
  (b) placing the test cell on a supporting surface with the plug resting on the supporting surface so that the larger-diameter end of the conical section is below its smaller-diameter end;

(c) resting a mold ring that is hollow and that has a cylindrical inside surface of diameter equal to the diameter of the smaller-diameter end of the conical section on top of and coaxial with the test cell to form an upward extension of it;

(d) filling the test cell and the mold ring completely full with the particulate material;

(e) placing a consolidation load container having an outside diameter slightly less than the inside diameter of the mold ring on top of the particulate material in the mold ring;

(f) consolidating the particulate material within the test cell and mold ring by applying a consolidation load $L_c$ uniformly distributed over the top of the particulate material in the mold ring by the consolidation load container, so that the direction of motion of the particulate material during consolidation is toward the plug, where $$L_c = \frac{1}{(1+m)} F\gamma_1 A_1 B$$

and
F = overpressure factor,
$\gamma_1$ = bulk density of the particulate material being tested,
$A_1$ = average cross sectional area of the test cell;

(g) continuing to apply the consolidation load for an interval of time equal to how long the particulate material in the full-size container has been at rest;

(h) removing the mold ring and the particulate material contained in it from the test cell;

(i) inverting the test cell with the plug and the consolidated particulate material still in it, so that after inversion the larger-diameter end of the conical section is above its smaller-diameter end;

(j) applying a gradually-increasing downward load to the plug to produce failure motion of the particulate material toward the smaller-diameter end of the conical section;

(k) noting the downward load $L_F$ at which failure occurs; and, (l) determining whether the noted load $L_F$ at which failure occurred is such that $$L_F \leq \left(\frac{B}{D} - 1\right) C A_1 \gamma_1$$

whereby, if it is, then flow from the full-size container will occur by gravity, but if it is not, then flow from the full size container will not occur by gravity, where D is the diameter of the larger-diameter end of the conical section.

7. A method of testing to determine the unconfined yield strength of a particulate material comprising the steps of:
(a) providing a test cell that is hollow and that includes a sleeve-like portion having an inside surface conforming to a frustrated conical section of height C, having a smaller-diameter end and a larger-diameter end, the test cell further including a plug spanning the larger-diameter end of the frustrated conical section and sized to fit loosely therein so as to be freely movable a limited distance into the spaced within the conical section and having a concave conical inwardly-facing surface;

(b) placing the test cell on a supporting surface with the plug resting on the supporting surface so that the larger-diameter end of the conical section is below its smaller-diameter end;

(c) filling the test cell completely full with the particulate material;

(d) consolidating the particulate material within the test cell by applying a downward pressure $\sigma_c$ at the smaller-diameter end of the conical section, so that the direction of motion of the particulate material during consolidation is toward the plug, where $$\sigma_c = (L_c/A_1) + \tfrac{1}{2}\gamma_1 C$$

and
$L_c$ = consolidation load
$A_1$ = average cross sectional area of the test cell
$\gamma_1$ = bulk density of the particulate material;

(e) inverting the test cell with the plug and the consolidated particulate material still in it, so that after the inversion the larger-diameter end of the conical section is above its smaller-diameter end;

(f) applying a gradually-increasing downward load to the plug to produce failure motion of the particulate material toward the smaller-diameter end of the conical section;

(g) noting the load $L_F$ at which failure occurs; and, (h) calculating the unconfined yield strength by the equation $$f_c = \frac{D}{h}\left(\gamma_1 + \frac{L_F}{A_1 C}\right)$$

where h = 2.1 for a conical test cell, and where D is the diameter of the larger-diameter end of the conical section.

8. Apparatus for use in determining the flow properties of a sample of a particulate matter comprising:
a hollow test cell including a sleeve-like portion having an inside surface conforming to a frustrated conical section and further including a plug spanning the larger-diameter end of the frustrated conical section, fitting loosely therein for unopposed movement a limited distance into the space within the conical section and having a concave conical surface coaxial with the axis of the conical section and facing toward the frustrated conical section.

9. The apparatus of claim 8 wherein the vertex semiangle of the conical section of the sleeve-like portion is in the range between a minimum of 4 degrees and a maximum of $\theta_c$, where $\theta_c$ is the largest angle compatable with the mass-flow stress field in the test cell.

10. A method of bench scale testing to determine the load at which unsupported consolidated particulate material arched over an outlet of width B in the bottom of a full-size container will fail by collapsing and flowing through the outlet, said method comprising the steps of:
(a) providing a test cell that is hollow and that includes a sleeve-like portion of rectangular cross section having an inside surface conforming to a frustrated wedge of height C, having a smaller end and a larger end, the test cell further including a plug spanning the larger end of the frustrated wedge and sized to fit loosely therein so as to be freely movable a limited distance into the space within the frustrated wedge and having a concave trough-like inwardly-facing surface;

(b) placing the test cell on a supporting surface with the plug resting on the supporting surface so that the larger end of the frustrated wedge is below its smaller end;

(c) filling the test cell completely full with particulate material;

(d) consolidating the particulate material within the test cell by applying a downward pressure at the smaller end of the frustrated wedge, so that the direction of motion on the particulate material during consolidation is toward the plug;

(e) inverting the test cell with the plug and the consolidated particulate material still in it, so that after the inversion the larger end of the frustrated wedge is above its smaller end;

(f) applying a gradually-increasing downward load to the plug to produce failure motion of the particulate material toward the smaller end of the frustrated wedge; and, (g) noting the downward load at which failure occurs.

11. The method of claim 10 wherein the step of consolidating the particulate material further comprises the step of applying a pressure to the particulate material at the smaller end of the frustrated wedge equal to $$\sigma_c = F\gamma_1 B$$

where
F=overpressure factor
$\gamma_1$=bulk density of the particulate material being tested, and
B=the width of the outlet of the full-size container.

12. The method of claim 11 wherein the pressure is applied to the particulate material for an interval of time equal to how long a particulate material in the full-size container has been at rest.

13. A method of bench scale testing to determine whether or not particulate material will flow, after having been at rest for some time, from a full-size container that requires gravity flow for discharge and that has an outlet of width B in its bottom, said method comprising the steps of:

(a) providing a test cell that is hollow and that includes a sleeve-like portion of rectangular cross section having an inside surface conforming to a frustrated wedge of height C, having a smaller end and a larger end, the test cell further including a plug spanning the larger end of the frustrated wedge and sized to fit loosely therein so as to be freely movable a limited distance into the space within the frustrated wedge and having a concave trough-like inwardly-facing surface;

(b) placing the test cell on a supporting surface with the plug resting on the supporting surface so that the larger end of the frustrated wedge is below its smaller end;

(c) filling the test cell completely full with particulate material;

(d) consolidating the particulate material within the test cell by applying a consolidation load $L_c$ uniformly distributed over the particulate material at the smaller end of the frustrated wedge, so that the direction of motion of the particulate material during consolidation is toward the plug, where $$L_c = F\gamma_1 A_1 B$$

where
F=overpressure factor,
$\gamma_1$=bulk density of the particulate material being tested,
$A_1$=average cross sectional area of the test cell;

(e) inverting the test cell with the plug and the consolidated particulate material still in it, so that after the inversion the larger end of the frustrated wedge is above its smaller end;

(f) applying a gradually-increasing downward load to the plug to produce failure motion of the particulate material toward the smaller end of the frustrated wedge;

(g) noting the downward load $L_F$ at which failure occurs; and, (h) determining whether the noted load $L_F$ at which failure occurred is such that $$L_F \leq \left(\frac{B}{D} - 1\right) CA_1\gamma_1$$

whereby, if it is, then flow from the full-size container will occur by gravity, but if it is not, then flow from the full-size container will not occur by gravity, where D is the width of the larger end of the test cell.

14. The method of claim 13 wherein the consolidation load $L_c$ is applied to the particulate material for an interval of time equal to how long a particulate material in the full-size container has been at rest.

15. A method of bench scale testing to determine whether or not particulate material will flow, after having been at rest for some time, from a full-size container that requires gravity flow for discharge and that has an outlet of width B in its bottom, said method comprising the steps of:

(a) providing a test cell that is hollow and that includes a sleeve-like portion of rectangular cross section having an inside surface conforming to a frustrated wedge of height C, having a smaller end and a larger end, the test cell further including a plug spanning the larger end of the frustrated wedge and sized to fit loosely therein so as to be freely movable a limited distance into the space within the frustrated wedge and having a concave trough-like inwardly-facing surface;

(b) placing the test cell on a supporting surface with the plug resting on the supporting surface so that the larger end of the frustrated wedge is below its smaller end;

(c) resting a mold frame that is hollow and that has a rectangular inside surface of dimensions equal to those of the smaller end of the frustrated wedge on top of and registered with the test cell of form an upward extension of it;

(d) filling the test cell and the mold frame completely full with the particulate material;

(e) placing a consolidation load container having outside dimensions slightly less than the inside dimensions of the mold frame on top of the particulate material in the mold frame;

(f) consolidating the particulate material within the test cell and mold frame by applying a consolidation load $L_c$ uniformly distributed over the top of the particulate material in the mold frame by the consolidation load container, so that the direction of motion of the particulate material during consolidation is toward the plug, where $$L_c = F \gamma_1 A_1 B$$

and

F = overpressure factor,
$\gamma_1$ = bulk density of the particulate material being tested, and
$A_1$ = average cross sectional area of the test cell;

(g) continuing to apply the consolidation load for an interval of time equal to how long the particulate material in the full-size container has been at rest;
(h) removing the mold frame and the particulate material contained in it from the test cell;
(i) inverting the test cell with the plug and the consolidated particulate material still in it, so that after inversion the larger end of the frustrated wedge is above its smaller end;
(j) applying a gradually-increasing downward load to the plug to produce failure motion of the particulate material toward the smaller end of the frustrated wedge;
(k) noting the downward load $L_F$ at which failure occurs; and,
(l) determining whether the noted load $L_F$ at which failure occurred is such that $$L_F \leq \left( \frac{B}{D} - 1 \right) C A_1 \gamma_1$$

whereby, if it is, then flow from the full-size container will occur by gravity, but if it is not, then flow from the full-size container will not occur by gravity, where D is the width of the larger end of the test cell.

16. A method of testing to determine the unconfined yield strength of a particulate material comprising the steps of:
(a) providing a test cell that is hollow and that includes a sleeve-like portion of rectangular cross section having an inside surface conforming to a frustrated wedge of height C, having a smaller end and a larger end, the test cell further including a plug spanning the larger end of the frustrated wedge and sized to fit loosely therein so as to be freely movable a limited distance into the space within the frustrated wedge and having a concave trough-like inwardly-facing surface;
(b) placing the test cell on a supporting surface with the plug resting on the supporting surface so that the larger end of the frustrated wedge is below its smaller end;
(c) filling the test cell completely full with particulate material;
(d) consolidating the particulate material within the test cell by applying a downward pressure $\theta_c$ at the smaller end of the frustrated wedge, so that the direction of motion of the particulate material during consolidation is toward the plug, where $$\sigma_c = L_C/A_1 + \gamma_1 C$$

and $L_c$ = consolidation load $A_1$ = average cross sectional area of the test cell and $\gamma_1$ = bulk density of the particulate material;
(e) inverting the test cell with the plug and the consolidated particulate material still in it, so that after the inversion the larger end of the frustrated wedge is above its smaller end;
(f) applying a gradually-increasing downward load to the plug to produce failure motion of the particulate material toward the smaller end of the frustrated wedge;
(g) noting the load $L_F$ at which failure occurs; and,
(h) calculating the unconfined yield strength by the equation $$f_c = \frac{D}{h} \left( \gamma_1 + \frac{L_F}{A_1 C} \right)$$

where $h = 1.1$ for a rectangular test cell, and where D is the width of the larger end of the test cell.

17. Apparatus for use in determining the flow properties of a sample of a particulate material comprising:
a hollow test cell including a sleeve-like portion of rectangular cross section having an inside surface conforming to a frustrated wedge and further including a plug spanning the larger end of the frustrated wedge and sized to fit loosely therein so as to be freely movable a limited distance into the space within the frustrated wedge and having a concave trough-like inwardly-facing surface.

18. The apparatus of claim 17 wherein the vertex semi-angle of the frustrated wedge of the sleeve-like portion is in the range between the minimum of 4 degrees and a maximum of $\theta_p$, where $\theta_p$ is the largest angle compatable with the mass-flow stress field in the test cell.

* * * * *